United States Patent [19]

Rice

[11] Patent Number: 4,581,753

[45] Date of Patent: Apr. 8, 1986

[54] TRANSLATIVELY DRIVEN X-RAY APERTURE MASK

[75] Inventor: Richard E. Rice, Arlington, Mass.

[73] Assignee: John K. Grady, Bittleton, Mass.

[21] Appl. No.: 653,081

[22] Filed: Sep. 21, 1984

[51] Int. Cl.$^4$ .............................................. G03B 41/16
[52] U.S. Cl. ..................................... 378/146; 378/150
[58] Field of Search .......................... 378/146, 150, 99

[56] References Cited

U.S. PATENT DOCUMENTS

| | | | |
|---|---|---|---|
| 4,403,338 | 9/1983 | Ruden | 378/146 |
| 4,404,591 | 9/1983 | Bonar | 378/146 |
| 4,534,051 | 8/1985 | Grady | 378/146 |
| 4,541,107 | 9/1985 | Rossi | 378/146 |

Primary Examiner—Craig E. Church
Attorney, Agent, or Firm—James H. Grover

[57] ABSTRACT

Scatter is reduced in an X-ray system by a relatively large light- or X-radiation-opaque mask rotating on a first axis and carrying smaller, radiation-opaque masks rotating off the first axis. The smaller masks have elongate radiation windows which are held parallel to each other and to a fixed plane through the first axis by translative drive and driven wheels on the larger and smaller masks coupled by a flexible linkage belt.

11 Claims, 3 Drawing Figures

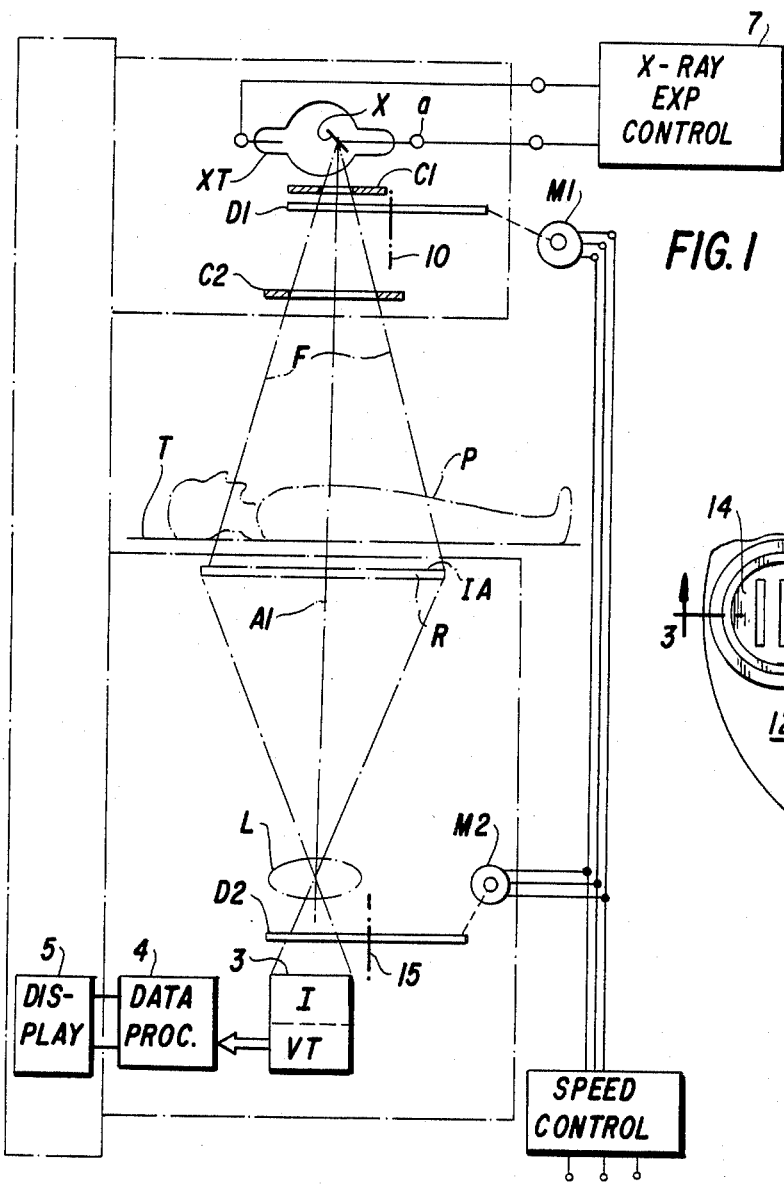
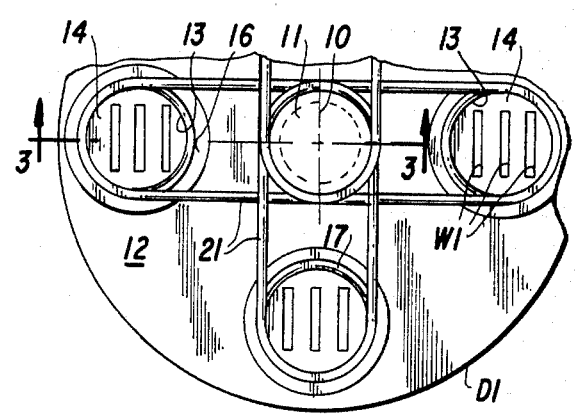
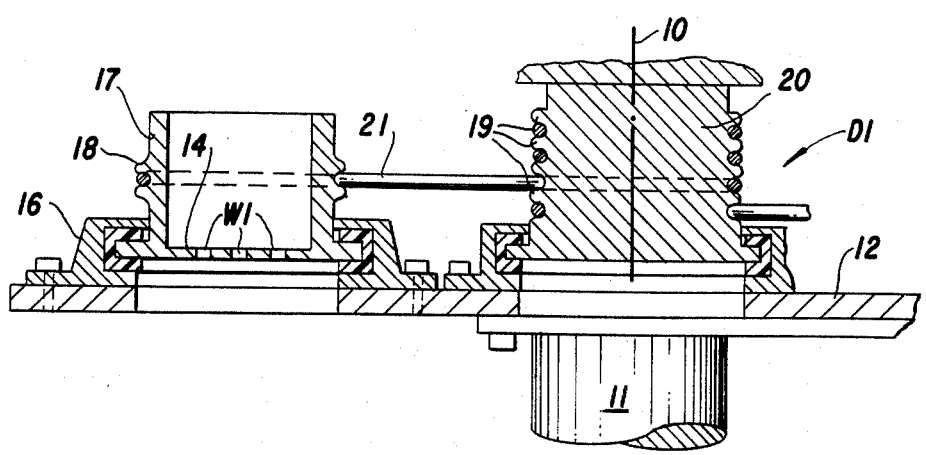
FIG. 1
FIG. 2
FIG. 3

TRANSLATIVELY DRIVEN X-RAY APERTURE MASK

BACKGROUND OF THE INVENTION

The present invention concerns X-ray apparatus for examination of a subject, as in radiological diagnosis of a human patient, and particularly X-ray systems in which X-ray radiation is partially masked during a scan of the subject. Systems of this general type are shown in U.S. Pat. Nos. 3,790,291, 4,315,146 and Radiology, 120: 705–711, September 1976. In such systems the X-radiation of the subject is masked by a moving radio-opaque body having a slit transmitting a fan-shaped beam from an X-ray tube source during one scan of the subject yielding one frame of X-ray image while reducing X-ray scatter from the subject.

It is one object of the present invention further to reduce the effect of X-ray scatter from the subject, and the consequent degradation of the X-ray shadow image, and also to improve the quality of the light image derived from the X-ray image.

SUMMARY OF THE INVENTION

The invention involves a moving mask for use in an X-ray system directing radiation from a source to an image area to produce an image frame at the area, the moving mask being between the source and the image area and comprising a relatively large radiation-opaque mask in the path rotating on a first axis outside the path and having a radiation-transparent zone; a relatively small radiation-opaque mask with an elongate radiation window, the small mask being mounted in the zone of the large mask to rotate on a second axis spaced from the first axis so that the window is periodically moved through the radiation path; and translative drive means coupling the large and small masks to hold the window parallel to a fixed plane through and coincident with the first axis. The moving mask may be between an X-ray tube source and an X-ray receptor producing secondary light, or between the X-ray receptor, as a source, and a light receptor for converting the light energy into a frame of electrical video signals. Thus the mask may be opaque to X-radiation or light radiation.

DRAWING

FIG. 1 is a schematic view of X-ray apparatus with moving masks according to the invention;
FIG. 2 is a plan view of a moving mask; and
FIG. 3 is a section on line 3—3 of FIG. 2.

DESCRIPTION

In the X-ray system of FIG. 1 the X-radiation source is the focal spot X on the anode a of an X-ray tube XT. The X-ray tube is energized by an electronic X-ray exposure control 7. From the source X a pyramidal or conical beam is directed along a radiation path on an axis A1 toward the position P of a human patient subject on an X-ray support table T. The beam is defined by X-ray-opaque collimators C1 and C2 and further restricted to a fan shaped beam F by an X-ray opaque mask formed by a disk D1 driven on an axis 10 by a motor M1 and which is the subject of the present invention.

The fan shaped X-ray beam F passes through the subject position P to an X-ray receptor R having an X-ray responsive image area or plane IA. Typically the receptor is a scintillation screen emitting visible light as secondary radiation corresponding to the received X-ray shadow image, and directed by a lens system L on a secondary, light-radiation path to the light image plane 3 of an electro-optical video system I, VT which converts the light image into electrical video signals. The video signals are applied through a data processor 4 to a display 5. Between the lens system L and light image plane 3 is a light mask consisting of a light-opaque disk D2 similar to the X-ray-opaque disk D1, and driven on an axis 15 by a second motor M2.

Either one or both of the disk shaped masks D1 or D2 may be in the form shown in FIGS. 2 and 3, mask D1 being composed of material such as lead which is X-radiation opaque and mask D2 being any light radiation opaque material. In each case the disk comprises a relatively large circular mask 12 mounted on a shaft 11 driven on a first axis 10 by one of the motors M1 or M2. The large mask 12 has four circular radiation-transparent zones 13 spaced ninety degrees apart. Above each zone 13 a relatively small radiation-opaque mask 14 is secured rotatively by a circular clamp 16 on the larger mask 12. A collar 17 extending upwardly from each of the small masks 14 has a sheave 18 rotatively coupled by a belt 21 to one of four sheaves 19 on a body 20 fixed in space. One or more light or X-ray transmissive windows W1 are linear and formed in parallel in each small mask, and the diameters of the sheaves on the collars 17 and the shaft 11 are equal so that as the shaft and large disk mask 12 rotate the parallel linear windows of all the small masks do not rotate in space but by translative motion remain parallel to each other and to a fixed plane through and coincident with the axis 10 of the shaft 11, that is, a plane in which the axis 10 lies.

By virtue of the translative motion of the slit apertures through the X-radiation or light path in the apparatus of FIG. 1 the radiation transmitted by each mask remains constant during each scan relative to the subject P.

It should be understood that the present disclosure is for the purpose of illustration only and that this invention includes all modifications and equivalents which fall within the scope of the appended claims.

I claim:

1. In an X-ray system directing X-radiation on a path through a subject position to an X-ray receptor, an X-ray scatter reducing device comprising:
   a relatively large radiation-opaque mask in the path rotating on a first axis outside the path and having a radiation-transparent zone;
   a relatively small radiation-opaque mask with an elongate radiation window, the small mask being mounted in the zone of the large mask to rotate on a second axis spaced from the first axis so that the window is periodically moved through the radiation path; and
   translative drive means coupling the large and small masks to hold the window parallel to a fixed plane through and coincident with the first axis.

2. A device according to claim 1 wherein a plurality of small masks are spaced equiangularly around the large mask and first axis, and coupled by translative drive means to the large mask.

3. A device according to claim 1 wherein the elongate window is of constant width throughout its length.

4. A device according to claim 1 wherein the small mask has a plurality of parallel windows.

5. A device according to claim 2 wherein each small mask has a plurality of windows, the windows of all masks being held parallel by the translative drive means.

6. A device according to claim 2 wherein each small mask comprises a driven wheel, the large mask having a drive wheel of the same diameter, and wherein the drive and driven wheels are coupled by a flexible linkage.

7. A system according to claim 1 wherein the small mask and large mask radiation-transparent zone are identical circularly so that the masks are continuously radio-opaque to the window.

8. A device according to claim 1 in combination with an X-ray source and X-ray receptor, the device being located between the source and receptor.

9. A combination according to claim 8 wherein the receptor comprises an X-ray responsive element producing light radiated on a secondary path.

10. A combination according to claim 9 including light responsive means on the secondary path and a light scatter reducing device between the X-ray receptor and light responsive device.

11. A combination according to claim 10 wherein the light scatter reducing device has small and large light-opaque masks.

* * * * *